United States Patent
Chang et al.

(10) Patent No.: US 7,800,651 B2
(45) Date of Patent: Sep. 21, 2010

(54) IMAGE-STABILIZATION DRIVING DEVICE

(75) Inventors: Shyang-Jye Chang, Hsinchu Hsien (TW); Yu-Jen Wang, Hsinchu Hsien (TW); Yi-Cheng Chen, Hsinchu Hsien (TW); Tai-Feng Wu, Hsinchu Hsien (TW)

(73) Assignee: Industrial Technology Research Institute, Hsinchu Hsien (TW)

( * ) Notice: Subject to any disclaimer, the term of this patent is extended or adjusted under 35 U.S.C. 154(b) by 388 days.

(21) Appl. No.: 11/966,771

(22) Filed: Dec. 28, 2007

(65) Prior Publication Data

US 2008/0100715 A1    May 1, 2008

(30) Foreign Application Priority Data

Oct. 4, 2007    (TW)    ............................... 96137209 A

(51) Int. Cl.
*H04N 5/228* (2006.01)
*H04N 5/232* (2006.01)
*G03B 17/00* (2006.01)

(52) U.S. Cl. ..................... 348/208.1; 348/345; 396/55

(58) Field of Classification Search ............. 348/208.1, 348/208.2, 209.4, 208.7, 219.1, 376, 345; 396/55–57
See application file for complete search history.

(56) References Cited

U.S. PATENT DOCUMENTS

| | | | | |
|---|---|---|---|---|
| 5,214,513 A | * | 5/1993 | Lee | 348/207.99 |
| 6,133,953 A | * | 10/2000 | Okada | 348/272 |
| 6,236,430 B1 | * | 5/2001 | Suzuki et al. | 348/219.1 |
| 6,967,677 B1 | * | 11/2005 | Gfeller | 348/208.99 |
| 7,161,621 B2 | * | 1/2007 | Kai et al. | 348/208.11 |
| 7,436,435 B2 | * | 10/2008 | Wada | 348/208.4 |
| 7,643,741 B2 | * | 1/2010 | Sekino | 396/55 |
| 2005/0052570 A1 | * | 3/2005 | Enomoto | 348/375 |

* cited by examiner

*Primary Examiner*—Lin Ye
*Assistant Examiner*—Trung Diep
(74) *Attorney, Agent, or Firm*—WPAT, P.C.; Anthony King

(57) ABSTRACT

Disclosed is an image-stabilization driving device including a first sliding member connected to an image sensor; a first piezoelectrical element for driving the first sliding member to move linearly along a first direction; a second sliding member connected to the first piezoelectrical element; and a second piezoelectrical element for driving the second sliding member to move linearly along a second direction intersecting with the first direction. The first and second piezoelectrical elements are adapted to drive the image sensor to move in a plane, thereby providing a structurally simple and miniaturized image-stabilization driving device.

25 Claims, 5 Drawing Sheets

IMAGE-STABILIZATION DRIVING DEVICE

BACKGROUND OF THE INVENTION

1. Field of the Invention

The present invention relates generally to a driving technique, and more particularly to an image-stabilization driving device capable of keeping image quality from being adversely affected by shake.

2. Description of Related Art

Optical systems and actuators applied in mobile phones or cameras have simple structures and small volume due to size limitation.

Along with wide application of mobile phone cameras nowadays, image quality of mobile phone cameras is expected to be same as that of digital cameras. For example, pixel number of mobile phone cameras has increased from 300,000 to 3,000,000. Meanwhile, in order to obtain preferred image quality, traditional fixed focal lens has been replaced by auto focus lens. In addition, optical zoom lens is integrated in mobile phone camera modules to replace digital zoom function that gives poor image quality. However, as mobile phones are light-weight and users generally operate mobile phones by single hand, image quality may usually be degraded by hand shake. Also, hand shake can easily occur when mobile phones are used indoors with poor lightness. Therefore, anti-hand shake mechanism is also needed in future mobile phones.

Although thin-type mobile phone cameras are easy to use, lens blur phenomenon can easily occur because of hand shake, especially when a person continuously takes photos during a long time and has poor hand force and stability. For example, blur image can occur due to tiny shake during zoom lens. Thus, an image-stabilization system is required to be integrated into optical system of thin-type mobile phones or cameras so as to provide anti-hand shake compensation function.

Compensation design for obtaining stabilized image quality has been proposed in such as US Publication Nos. 2003067544, No. 2006056829, U.S. Pat. No. 5,768,016, JP Publication Nos. 2003111444 and No. 2004241922. For example, a smooth impact drive mechanism (SIDM) integrated to a lens module is proposed by WADA etc. in Minolta Corporation, wherein two piezoelectrical actuators are used to control coordinate position (X, Y) of an image sensor in a plane, thereby stabilizing image quality. US Publication No. 20060056829 discloses a smooth impact drive mechanism comprising a stacked three-layer metal frames, which however has complicated components and accordingly has complicated assembly process and cannot meet the requirement of module miniaturization. Moreover, the present optical stabilization systems are mainly aimed at digital cameras and cannot meet requirement of mobile phone cameras.

Therefore, there exists a strong need to provide an image-stabilization driving device that is miniaturized and has simple structure and is easy to fabricate and assemble so as to overcome the above-mentioned drawbacks.

SUMMARY OF THE INVENTION

According to the above drawback, an objective of the present invention is to provide an image-stabilization driving device having simple structure.

Another objective of the present invention is to provide a miniaturized image-stabilization driving device.

A further objective of the present invention is to provide an image-stabilization driving device that is easy to fabricate and assemble.

In order to attain the above and other objectives, the present invention provides an image-stabilization driving device for driving an image sensor to move in a plane relative to a substrate, the image-stabilization driving device comprises a first sliding member connected to an image sensor, the first sliding member having a first elastic holding portion at bottom thereof; a first piezoelectrical element having first holding surfaces to be elastically held by the first elastic holding portion so as to drive the first sliding member to move linearly along a first direction; a second sliding member connected to the first piezoelectrical element, the second sliding member having a second elastic holding portion at bottom thereof; and a second piezoelectrical element connected to the substrate, the second piezoelectrical element having second holding surfaces to be elastically held by the second elastic holding portion so as to drive the second sliding member to move linearly along a second direction intersecting with the first direction.

In the above-described image-stabilization driving device, the first sliding member can further comprise an elastic sheet, and the first elastic holding portion can comprise bending segments formed at two sides of the elastic sheet and engaging structures formed at bottom of the bending segments for holding the first holding surfaces. In principle, the engaging structures should contact and hold the first holding surfaces and can smoothly move, which can be such as curling edges, columns or slide rails formed at bottom of the bending segments. The first piezoelectrical element at least comprises a piezoelectrical ceramic sheet, and the first holding surfaces are disposed at sides of the piezoelectrical ceramic sheet and parallel to the first direction. Preferably, the first holding surfaces have one of a V-shaped section and an arc-shaped section. The first piezoelectrical element can further comprise a first electrode formed on one surface of the piezoelectrical ceramic sheet, and a second electrode and a third electrode symmetrically formed on an opposed surface of the piezoelectrical ceramic sheet. Preferably, the first electrode is a negative electrode, and the second and third electrodes are positive electrodes.

The second sliding member further comprises an elastic sheet, and the second elastic holding portion comprises bending segments formed at two sides of the elastic sheet and engaging structures formed at bottom of the bending segments for holding the second holding surfaces. In principle, the engaging structures should contact and hold the second holding surfaces and can smoothly move, which can be such as curling edges, columns or slide rails formed at bottom of the bending segments. The second piezoelectrical element at least comprises a piezoelectrical ceramic sheet, and the second holding surfaces are disposed at sides of the piezoelectrical ceramic sheet and parallel to the second direction. Preferably, the second holding surfaces have one of a V-shaped section and an arc-shaped section. The second piezoelectrical element can further comprise a first electrode formed on one surface of the piezoelectrical ceramic sheet, and a second electrode and a third electrode symmetrically formed on an opposed surface of the piezoelectrical ceramic sheet. Preferably, the first electrode is a negative electrode, and the second and third electrodes are positive electrodes.

The image-stabilization driving device according to the present invention can further comprise a position sensor for sensing displacement of the image sensor in the plane. Preferably, the position sensor is one of a magnetic type sensor, a capacitor type sensor and an optical type sensor. The position sensor can comprise a magnetic element and a Hall element respectively coupled to the image sensor and the substrate.

The image-stabilization driving device according to the present invention drives an image sensor through two intersecting piezoelectrical elements and two integrated sliding members. Compared with conventional complicated structure and big volume of multi-layer metal frames and piezoelectrical actuators, the present invention achieves a simple and miniaturized structure, which can be easily applied in electronic devices such as mobile phones. Further, the two piezoelectrical elements and the two sliding members have no complicated design and can be integrally formed or formed through elements of general specification, thereby facilitating fabrication and assembly.

DETAILED DESCRIPTION OF PREFERRED EMBODIMENTS

The following illustrative embodiments are provided to illustrate the disclosure of the present invention, these and other advantages and effects can be apparent to those skilled in the art after reading the disclosure of this specification.

Figure 1:
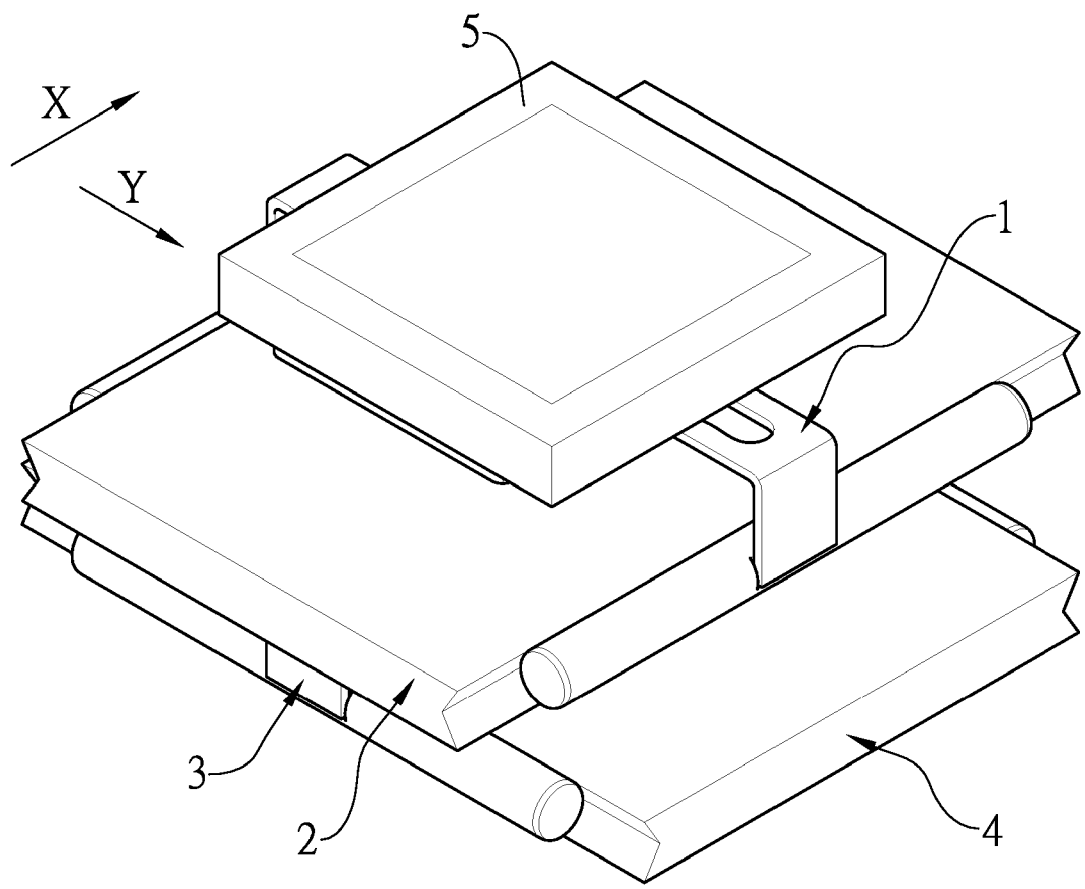
FIG. 1 is a diagram of an image-stabilization driving device according to a preferred embodiment of the present invention.
Figure 2:
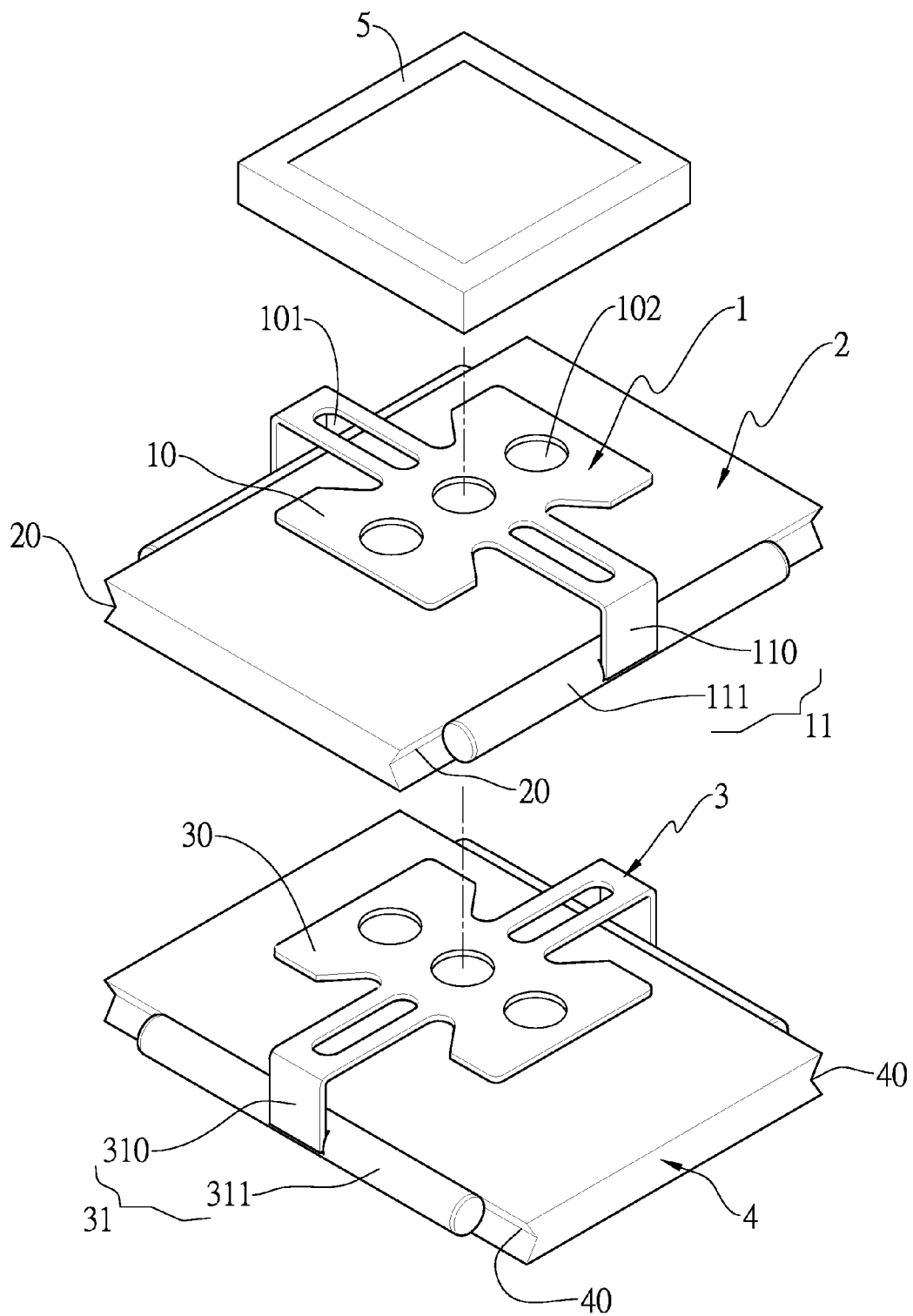
FIG. 2 is an exploded diagram of FIG. 1.
Figure 3A:
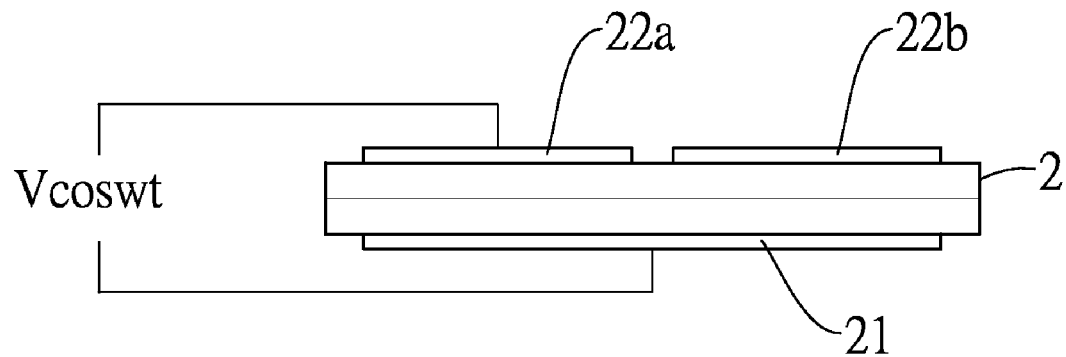
FIGS. 3A and 3B are diagrams showing two driving states when the first piezoelectrical element of the image-stabilization driving device is connected to a driving circuit.
Figure 3B:
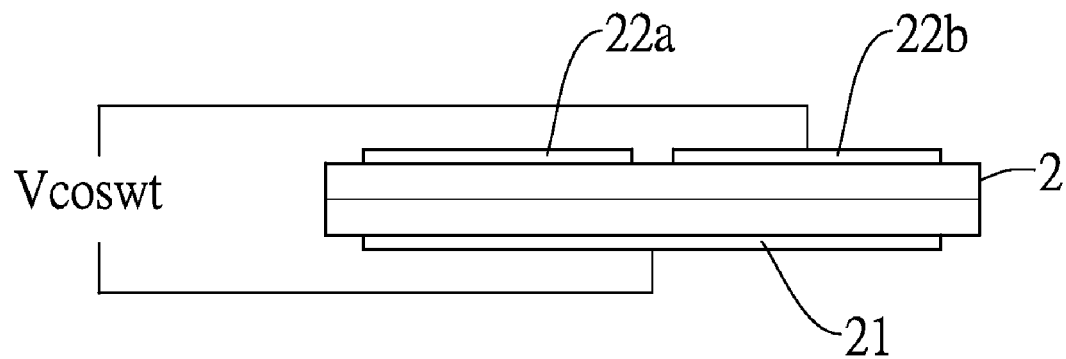

Referring to FIGS. 1 and 2, an image-stabilization driving device is proposed, which is used to drive an image sensor 5 to move in a plane. The image-stabilization driving device comprises a first sliding member 1 connected to the image sensor 5, a first piezoelectrical element 2 for driving the first sliding member 1 to move linearly along a first direction X, a second sliding member 3 connected to the first piezoelectrical element 2, and a second piezoelectrical element 4 for driving the second sliding member 3 to move linearly along a second direction Y intersecting with the first direction X. Thus, the image sensor can be driven to move in a plane through the first piezoelectrical element 2 and the second piezoelectrical element 4, and a structurally simple and miniaturized image-stabilization driving device is provided.

The bottom of the first sliding member 1 has a first elastic holding portion 11 for elastically holding the first piezoelectrical element 2 and the top of the first sliding member 1 is connected to the image sensor 5. The image sensor 5 can be of a CCD (Charge Coupled Device) type or a CMOS type. The first sliding member 1 has a size substantially equal to that of the image sensor 5. The first sliding member 1 has a size approximately equal to that of the image sensor 5, and in principle the first sliding member 1 should be sufficiently connected to the image sensor 5 and there is no special limit.

In the present embodiment, the first sliding member 1 comprises a planar elastic sheet 10. The first elastic holding portion 11 comprises bending segments 110 formed at two sides of the elastic sheet 10 and engaging structures 111 formed at bottom of the bending segments 110. The bending segments 110 have a characteristic of elastic deformation and the first piezoelectrical element 2 is held by the engaging structures 111. In addition, the first sliding member 1 can be connected to the image sensor 5 through adhering. In order to facilitate adhering the first sliding member 1 to the image sensor 5 through a dispensing method, a positioning structure 102 can be pre-disposed on surface of the elastic sheet 10. In the present embodiment, the positioning structure 102 is through holes formed in the elastic sheet 10, but it is not limited thereto. Further, to increase flexibility or meet light weight requirement, a flexible structure 101 can be pre-disposed on surface of the elastic sheet 10. In the present embodiment, the elastic sheet 10 is openings formed in the elastic sheet 10. Of course, the positioning structure 102 and the flexible structure 101 are not absolutely necessary and can be omitted in other embodiments. Alternatively, the elastic sheet 101 may have a rectangular shape and the positioning structure 102 and the flexible structure 101 may be integrated into one structure such as a positioning structure 102 having flexible function or a flexible structure 101 having positioning function.

The first piezoelectrical element 2 has first holding surfaces 20 to be elastically held by the first elastic holding portion 11 of the first sliding member 1 so as to drive the first sliding member 1 as well as the image sensor 5 to move linearly in the first direction X. In the present embodiment, the first piezoelectrical element 2 is a piezoelectrical ceramic sheet with the polarization direction parallel to its thickness direction. The first holding surfaces 20 are disposed at sides of the piezoelectrical ceramic sheet and parallel to the first direction X. Preferably, width of the first piezoelectrical element 2 is slightly bigger than spacing between the two engaging structures 111 such that a suitable prestress can be provided when the engaging structures 111 contact and hold the first holding surfaces 20 at two sides of the first piezoelectrical element 2.

In addition, to make the engaging structures 111 capable of elastically holding the first holding surfaces 20 in the first direction X, the first holding surfaces 20 have a V-shaped section, which however is not limited thereto. In other embodiment, the first holding surfaces 20 can have an arc-shaped section. The first piezoelectrical element 2 of a piezoelectrical ceramic sheet can further comprise a first electrode 21 formed on a surface of the piezoelectrical ceramic sheet, and a second electrode 22a and a third electrode 22b symmetrically formed on an opposed surface of the piezoelectrical ceramic sheet. In the present embodiment, the first electrode 21 is a negative electrode, and the second electrode 22a and the third electrode 22b are positive electrodes. By applying voltage such as a driving voltage of sinuous waveform or square waveform to the first electrode 21 and the second electrode 21a, a converse piezoelectrical effect causes the first piezoelectrical element 2 to generate mechanical energy of high-frequency swing, which further drives the first sliding member 1 to move in the first direction X. On the other hand, when voltage is applied to the first electrode 21 and the third electrode 21b, the first sliding member 1 is driven to move in a direction reverse to the first direction X.

Bottom of the second sliding member 3 has a second elastic holding portion 31 for elastically holding the second piezoelectrical element 4, and top of the second sliding member 3 is connected to the first piezoelectrical element 2. Size and structure design of the second sliding member 3 are same as that of the first sliding member 1, except that the disposing direction of the second sliding member 3 intersects with that of the first sliding member 1. Other structures such as the elastic sheet 30, bending segments 310 and engaging structures 311 of the second elastic holding portion 31 and even flexible structure and positioning structure are same as that of the first sliding member 1 and thus detailed description thereof is omitted.

The second piezoelectrical element 4 has second holding surfaces 40 to be elastically held by the second elastic holding portion 31 of the second sliding member 3 so as to drive the second sliding member 3 as well as the first piezoelectrical element 2 to move linearly in a second direction Y. Size and structure design of the second piezoelectrical element 4 are same as that of the first piezoelectrical element 2, except that the disposing direction of the second piezoelectrical element 4 intersects with that of the first piezoelectrical element 2, and detailed description thereof is omitted.

Figure 4:
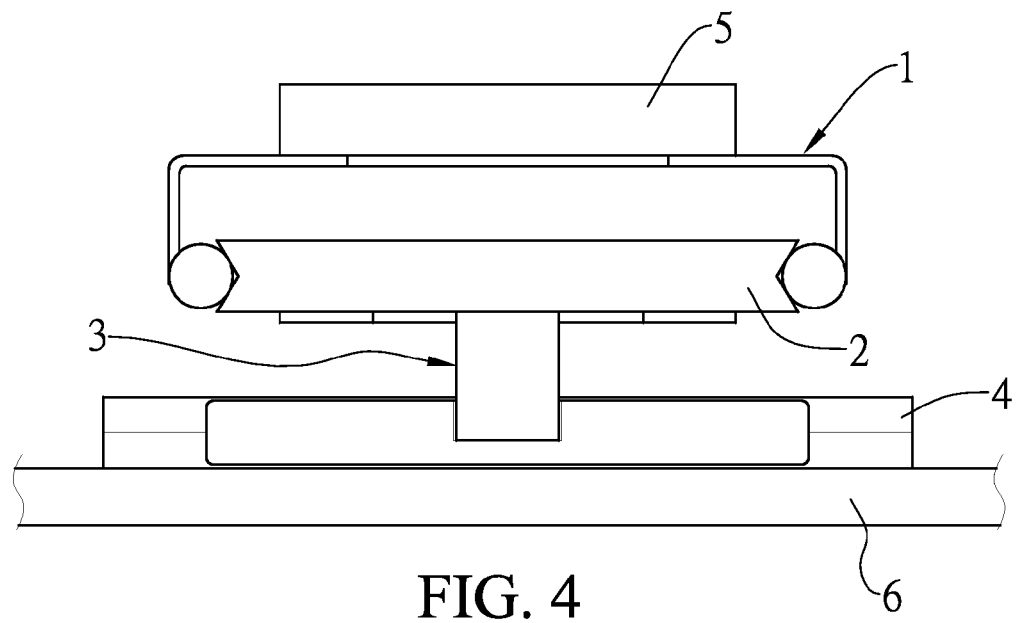
FIG. 4 is a side view of the image-stabilization driving device integrated to a substrate.

As shown in FIG. 4, the image-stabilization driving device according to the present invention can be integrated to a substrate 6 in practical use. In particular, the second piezoelectrical element 4 is connected to surface of the substrate 6 such that the image sensor 5 can be driven to move in a plane relative to the substrate 6 through the first piezoelectrical element 2 and the second piezoelectrical element 4. In the present embodiment, the substrate 6 is a circuit board already existing in an image capture device, which however is not limited thereto. In other embodiments, the substrate 6 may be casing of an image capture device.

Figure 5A:
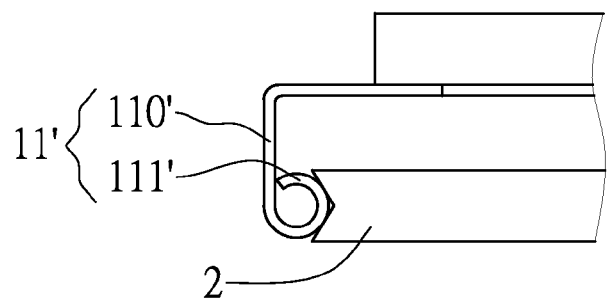
FIGS. 5A and 5B are diagrams showing two kinds of engaging structures of the image-stabilization driving device according to the present invention.
Figure 5B:
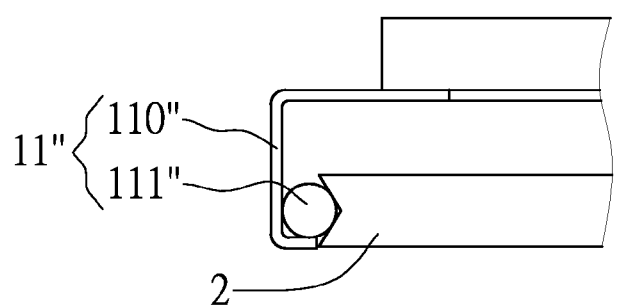

The above-described first elastic holding portion 11 of the first sliding member 1 comprises bending segments 110 formed at two sides of the elastic sheet 10 and engaging structures 111 formed at bottom of the bending segments 110. The bending segments 110 can be integrally formed with the elastic sheet 10 and columns made of such as copper can be connected to the bottom of the bending segment 110 so as to form engaging structures 111. In principle, the engaging structures 111 should hold the first holding surfaces 20 and can smoothly move. For example, as shown in FIG. 5A, the engaging structures 111' of curling edges are integrally formed with the bending segments 110'. Alternatively, as shown in FIG. 5B, the engaging structures 111' of slide rails are formed at bottom of the bending segments 110'. Of course, the second elastic holding portion 31 of the second sliding member 3 can have same variation and detailed description thereof is omitted.

Figure 6:
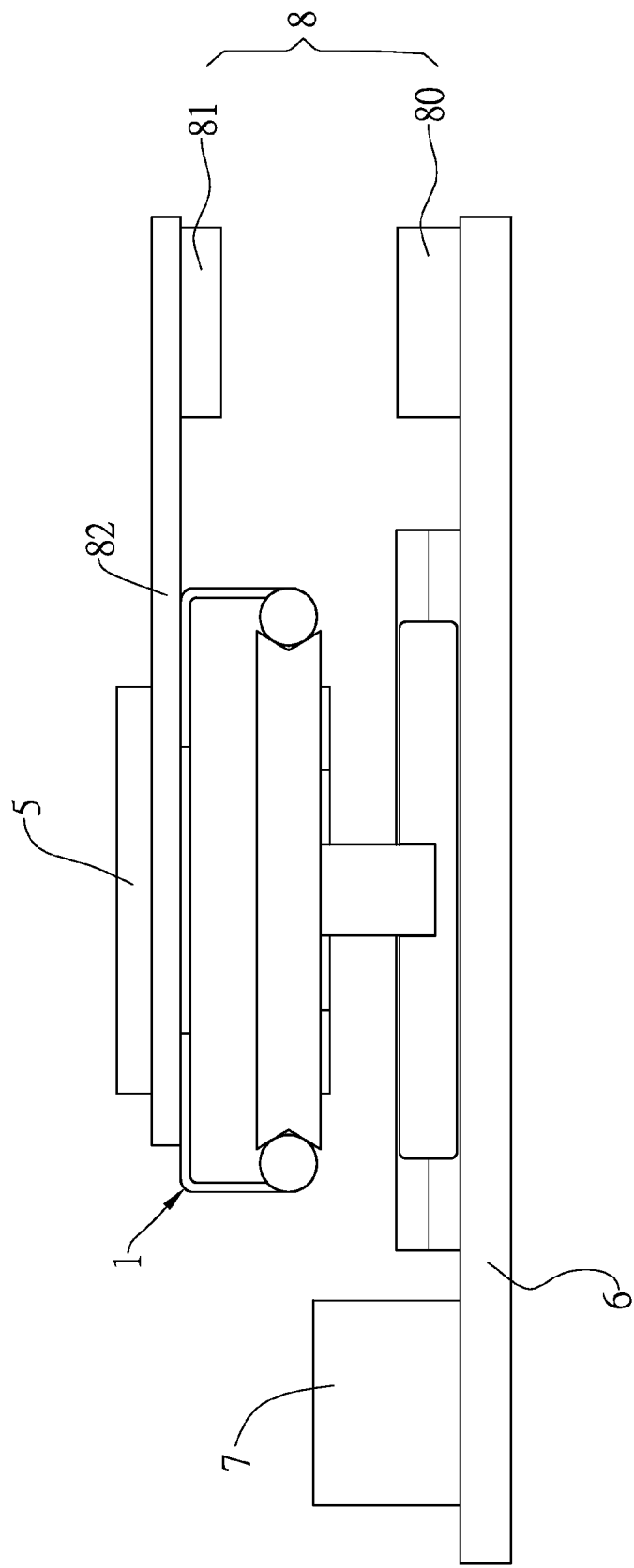
FIG. 6 is a diagram showing an image-stabilization driving device with a position sensor integrated therein.

As shown in FIG. 6, the image-stabilization driving device can further be integrated with a vibration sensor 7 disposed on the substrate 6 for sensing external vibration or be integrated with a position sensor 8 for sensing displacement of the image sensor 5 in a plane. The sensed information can then be used in feedback control. The position sensor 8 can be a magnetic type sensor, a capacitor type sensor or an optical type sensor. In the present embodiment, the position sensor 8 comprises a magnetic element 81 coupled to the image sensor 5, and a Hall element 80 coupled to the substrate 6, wherein the magnetic element 81 is pre-connected to an extending sheet 82 and the extending sheet 82 is then disposed between the image sensor 5 and the first sliding member 1. In other embodiments, the magnetic element 81 can be directly connected to one side of the image sensor 5.

Therefore, the image-stabilization driving device according to the present invention drives an image sensor through two intersecting piezoelectrical elements and two integrated sliding members. Compared with conventional complicated structure and big volume of multi-layer metal frames and piezoelectrical actuator, the present invention achieves a simple and miniaturized structure, which can be easily applied in electronic devices such as mobile phones. Further, the two piezoelectrical elements and the two sliding members have no complicated design and can be integrally formed or formed through elements of general specification, thereby facilitating fabrication and assembly.

The above-described descriptions of the detailed embodiments are only to illustrate the preferred implementation according to the present invention, and it is not to limit the scope of the present invention, Accordingly, all modifications and variations completed by those with ordinary skill in the art should fall within the scope of present invention defined by the appended claims.

What is claimed is:

1. An image-stabilization driving device for driving an image sensor to move in a plane relative to a substrate, the image-stabilization driving device comprising:
    a first sliding member connected to an image sensor, the first sliding member having a first elastic holding portion at bottom thereof and an elastic sheet;
    a first piezoelectrical element having first holding surfaces to be elastically held by the first elastic holding portion so as to drive the first sliding member to move linearly along a first direction;
    a second sliding member connected to the first piezoelectrical element, the second sliding member having a second elastic holding portion at bottom thereof; and
    a second piezoelectrical element connected to the substrate, the second piezoelectrical element having second holding surfaces to be elastically held by the second elastic holding portion so as to drive the second sliding member to move linearly along a second direction intersecting with the first direction,
    wherein the first elastic holding portion comprises bending segments formed at two sides of the elastic sheet and engaging structures formed at bottom of the bending segments for holding the first holding surfaces, and the engaging structures are selected from the group consisting of curling edges, columns and slide rails.

2. The image-stabilization driving device of claim 1, wherein the first piezoelectrical element at least comprises a piezoelectrical ceramic sheet, and the first holding surfaces are disposed at sides of the piezoelectrical ceramic sheet and parallel to the first direction.

3. The image-stabilization driving device of claim 2, wherein the first holding surfaces have one of a V-shaped section and an arc-shaped section.

4. The image-stabilization driving device of claim 2, wherein the first piezoelectrical element further comprises a first electrode formed on one surface of the piezoelectrical ceramic sheet, and a second electrode and a third electrode symmetrically formed on an opposed surface of the piezoelectrical ceramic sheet.

5. The image-stabilization driving device of claim 4, wherein the first electrode is a negative electrode, the second electrode and the third electrode are positive electrodes.

6. The image-stabilization driving device of claim 1, wherein the elastic sheet comprises a flexible structure.

7. The image-stabilization driving device of claim 6, wherein the flexible structure is an opening formed in the elastic sheet.

8. The image-stabilization driving device of claim 1, wherein the elastic sheet comprises a positioning structure.

9. The image-stabilization driving device of claim 8, wherein the positioning structure is a through hole formed in the elastic sheet.

10. The image-stabilization driving device of claim 1, wherein the second sliding member further comprises an elastic sheet, and the second elastic holding portion comprises bending segments formed at two sides of the elastic sheet and engaging structures formed at bottom of the bending segments for holding the second holding surfaces.

11. The image-stabilization driving device of claim 10, wherein the engaging structures are curling edges formed at bottom of the bending segments.

12. The image-stabilization driving device of claim 10, wherein the engaging structures are columns formed at bottom of the bending segments.

13. The image-stabilization driving device of claim 10, wherein the engaging structure are slide rails formed at bottom of the bending segments.

14. The image-stabilization driving device of claim 10, wherein the second piezoelectrical element at least comprises a piezoelectrical ceramic sheet, and the second holding surfaces are disposed at sides of the piezoelectrical ceramic sheet and parallel to the second direction.

15. The image-stabilization driving device of claim 14, wherein the second holding surfaces have one of a V-shaped section and an arc-shaped section.

16. The image-stabilization driving device of claim 14, wherein the second piezoelectrical element further comprises a first electrode formed on one surface of the piezoelectrical ceramic sheet, and a second electrode and a third electrode symmetrically formed on an opposed surface of the piezoelectrical ceramic sheet.

17. The image-stabilization driving device of claim 16, wherein the first electrode is a negative electrode, the second electrode and the third electrode are positive electrodes.

18. The image-stabilization driving device of claim 10, wherein the elastic sheet comprises a flexible structure.

19. The image-stabilization driving device of claim 18, wherein the flexible structure is an opening formed in the elastic sheet.

20. The image-stabilization driving device of claim 10, wherein the elastic sheet comprises a positioning structure.

21. The image-stabilization driving device of claim 20, wherein the positioning structure is a through hole formed in the elastic sheet.

22. The image-stabilization driving device of claim 1 further comprising a position sensor for sensing displacement of the image sensor in the plane.

23. The image-stabilization driving device of claim 22, wherein the position sensor is one of a magnetic type sensor, a capacitor type sensor and an optical type sensor.

24. The image-stabilization driving device of claim 22, wherein the position sensor comprises a magnetic element and a Hall element respectively coupled to the image sensor and the substrate.

25. The image-stabilization driving device of claim 1 further comprising a vibration sensor disposed on the substrate for sensing external vibration.

\* \* \* \* \*